US009918920B2

(12) United States Patent
Tsutsui et al.

(10) Patent No.: US 9,918,920 B2
(45) Date of Patent: Mar. 20, 2018

(54) ORAL COMPOSITION

(71) Applicant: Kao Corporation, Chuo-ku, Tokyo (JP)

(72) Inventors: Sei Tsutsui, Yokohama (JP); Atsushi Yamagishi, Kashiwa (JP); Yoshiyuki Eshita, Tokyo (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/316,737

(22) PCT Filed: Jun. 5, 2015

(86) PCT No.: PCT/JP2015/066282
§ 371 (c)(1),
(2) Date: Dec. 6, 2016

(87) PCT Pub. No.: WO2015/190402
PCT Pub. Date: Dec. 17, 2015

(65) Prior Publication Data
US 2017/0196794 A1    Jul. 13, 2017

(30) Foreign Application Priority Data

Jun. 10, 2014  (JP) .................................. 2014-119930

(51) Int. Cl.
| | | |
|---|---|---|
| A61K 8/55 | (2006.01) | |
| A61K 8/24 | (2006.01) | |
| A61K 8/34 | (2006.01) | |
| A61K 8/22 | (2006.01) | |
| A61K 8/25 | (2006.01) | |
| A61K 8/19 | (2006.01) | |
| A61K 8/46 | (2006.01) | |
| A61K 8/73 | (2006.01) | |
| A61K 8/86 | (2006.01) | |
| A61K 8/60 | (2006.01) | |
| A61Q 11/00 | (2006.01) | |

(52) U.S. Cl.
CPC ................. A61K 8/55 (2013.01); A61K 8/19 (2013.01); A61K 8/22 (2013.01); A61K 8/24 (2013.01); A61K 8/25 (2013.01); A61K 8/345 (2013.01); A61K 8/463 (2013.01); A61K 8/60 (2013.01); A61K 8/73 (2013.01); A61K 8/731 (2013.01); A61K 8/86 (2013.01); A61Q 11/00 (2013.01); A61K 2800/28 (2013.01)

(58) Field of Classification Search
CPC ....................................................... A61K 8/34
USPC ..................................................... 424/49, 52
See application file for complete search history.

(56) References Cited

U.S. PATENT DOCUMENTS 4,263,276 A * 4/1981 Harvey ..................... A61K 8/21
424/52
4,335,102 A * 6/1982 Nakashima .............. A61K 8/19
424/48
4,394,371 A * 7/1983 Barberio ................... A61K 8/24
206/524.1
8,580,234 B2   11/2013  Isobe et al.
9,168,213 B2   10/2015  Isobe et al.
2010/0086498 A1* 4/2010 Haught ..................... A61K 8/19
424/49
2011/0223119 A1   9/2011  Isobe et al.
2014/0017180 A1   1/2014  Isobe et al.
2015/0297479 A1  10/2015  Nakauchi et al.

FOREIGN PATENT DOCUMENTS

| CN | 101690699 A | 4/2010 |
|---|---|---|
| CN | 102670457 A | 9/2012 |
| JP | 61-200905 A | 9/1986 |
| JP | 2003-335646 A | 11/2003 |
| JP | 2009-263281 A | 11/2009 |
| JP | 2010-150225 A | 7/2010 |
| JP | 2012-219058 A | 11/2012 |
| JP | 5508611 B1 | 6/2014 |

(Continued)

OTHER PUBLICATIONS

International Search Report (ISR) for PCT/JP2015/066282; I.A. fd Jun. 5, 2015, dated Sep. 8, 2015 from the Japan Patent Office, Tokyo, Japan.

(Continued)

*Primary Examiner* — Walter Webb
(74) *Attorney, Agent, or Firm* — Sterne, Kessler, Goldstein & Fox P.L.L.C.

(57) ABSTRACT

The present invention relates to a dentifrice composition which removes a fine stain and a stain adhering to the surface of teeth sufficiently, enhances the whitening effect on teeth and the gloss-imparting effect on teeth, also increases the amount of fluorine adsorption to teeth, and decreases the feeling of astringency. The oral composition of the present invention comprises the following component (A): phytic acid or an alkali metal salt thereof in an amount of 0.04% by mass or more and 1% by mass or less in terms of phytic acid; and component (B): monofluorophosphoric acid or an alkali metal salt thereof in an amount of 500 ppm or more and 1500 ppm or less in terms of fluorine atoms, wherein a mass ratio of the component (A) to the component (B), ((A)/(B)), is 0.1 or more and 1.4 or less, and a fluoride ion-supplying compound (F) selected from the group consisting of sodium fluoride, potassium fluoride and ammonium fluoride, a polyvalent metal cation, and a polyphosphoric acid or a salt thereof are comprised in a limited amount, and the pH thereof is from 5.5 to 6.5.

13 Claims, 1 Drawing Sheet

(56) References Cited

FOREIGN PATENT DOCUMENTS

JP        2014-125425 A    7/2014
WO     WO 02/02060 A2    1/2002

OTHER PUBLICATIONS

International Preliminary Report on Patentability (IPRP), Chapter I of the Patent Cooperation Treaty, including the Written Opinion for PCT/JP2015/066282; I.A. fd Jun. 5, 2015, dated Dec. 15, 2016, by the International Bureau of WIPO, Geneva, Switzerland.
The extended European search report, including the supplementary European search report and the European search opinion, for EP Appl. No. 15807170.4, dated Dec. 5, 2017, European Patent Office, Munich, Germany.
Database GNPD[Online] MINTEL; Aug. 2014 "Spearmint flavoured Anti-cavity and whitening toothpaste with xylitol," XP002775763, Database accession No. 2589257.

* cited by examiner

ORAL COMPOSITION

FIELD OF THE INVENTION

The present invention relates to an oral composition.

BACKGROUND OF THE INVENTION

Human teeth are stained by adhesion of various staining substances, in addition to calculus and plaque, on the surfaces thereof, and are decreased in gloss. Such staining and a decrease in gloss are demanded to be prevented as much as possible also in terms of beauty. In order to solve such a problem, there have been developed various oral compositions in which phytic acid which is known to exert a removing effect on tobacco tar, a suppressing effect on calculus, and the like is used.

For example, Patent Literature 1 discloses an oral composition in which a specific amount of a phytic acid or a salt thereof and a specific amount of pyrophosphoric acid or a salt thereof are contained in combination in a specific mass ratio, and the composition rapidly removes a minute stain adhering to the surface of teeth to exert an excellent gloss-imparting effect. In addition, Patent Literature 2 discloses a composition for use in removal of a solid product, in which phytic acid or a salt thereof is contained in a specific amount and also the content of a polyvalent cation is restrained, and such a composition can have an excellent whitening effect on teeth and also impart gloss to teeth.

On the other hand, phytic acid tends to exhibit an increased feeling of astringency depending on the amount thereof, and may also result in deterioration in feeling upon use. In view of the circumstances, for example, Patent Literature 3 discloses a dentifrice composition in which phytic acid or a salt thereof and a specific organic resin powder are contained in combination in respective specific amounts, and the feeling of astringency derived from phytic acid is effectively planned to be decreased while an excellent whitening effect on teeth is retained. Moreover, Patent Literature 4 discloses a dentifrice composition which contains a phytic acid salt, a pyrophosphoric acid salt, a monofluorophosphoric acid salt and the like in respective specific amounts, to thereby enable to exert a cleaning effect on teeth and a whitening effect on teeth.

(Patent Literature 1) JP-A-2012-219058
(Patent Literature 2) JP-A-2010-150225
(Patent Literature 3) JP-A-2009-263281
(Patent Literature 4) CN-A-101690699

SUMMARY OF THE INVENTION

The present invention relates to an oral composition comprising the following components (A) and (B):

(A) phytic acid or an alkali metal salt thereof in an amount of 0.04% by mass or more and 1% by mass or less in terms of phytic acid; and (B) monofluorophosphoric acid or an alkali metal salt thereof in an amount of 500 ppm or more and 1,500 ppm or less in terms of fluorine atoms, wherein a mass ratio of the component (A) to the component (B), ((A)/(B)), is 0.1 or more and 1.4 or less, the composition does not comprise or comprises (F) a fluoride ion-supplying compound selected from the group consisting of sodium fluoride, potassium fluoride and ammonium fluoride in an amount of 100 ppm or less in terms of fluorine atoms, the composition does not comprise or comprises a polyvalent metal cation in an amount of less than 0.1-fold mol relative to the component (A), the composition does not comprise or comprises polyphosphoric acid or a salt thereof in an amount of 20% by mass or less in terms of acid relative to the component (A), and the pH thereof is from 5.5 to 6.5.

DETAILED DESCRIPTION OF THE INVENTION

Figure 1:
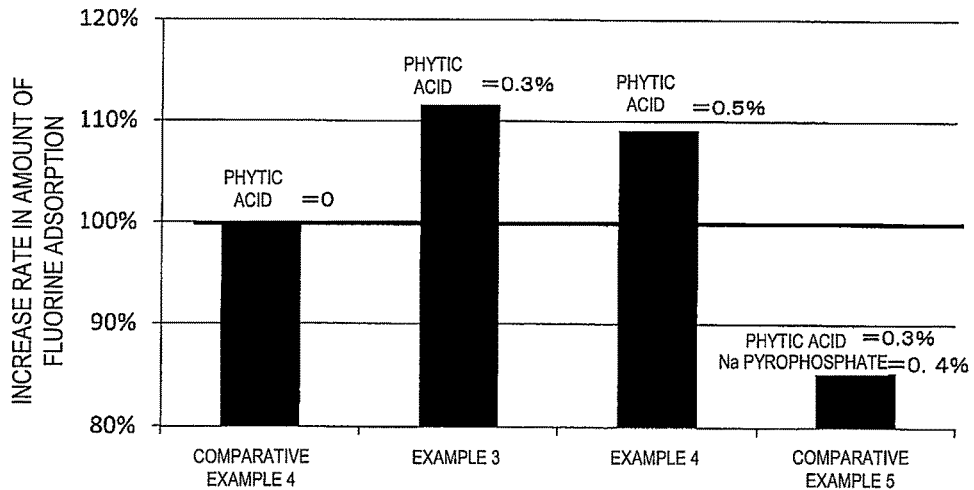
FIG. 1 is a graph illustrating an increase rate in amount of fluorine adsorption in each of Examples 3 to 4 and Comparative Examples 4 to 5 based on that in Comparative Example 4.

In general, a compound which can supply a fluoride ion is known to be effective for preventing dental caries from being developed because a fluoride ion released is incorporated into dental enamel or dentine to produce calcium fluoride.

If the compound which can supply a fluoride ion is excessively present in a phytic acid-containing composition, however, the whitening effect and the gloss-imparting effect of phytic acid tend to be impaired, and therefore it is desirable in all of Patent Literatures 1 to 3 to restrain the content of such a compound as much as possible. Therefore, an oral composition which can allow fluorine to effectively adsorb to teeth while sufficiently exerting the effects of phytic acid is not still realized.

In addition, when a pyrophosphoric acid salt is contained in the amount described in Patent Literature 4 in the coexistence of the phytic acid-containing composition and the compound which can supply a fluoride ion, the effect of fluorine adsorption to teeth may also be further decreased and therefore additional studies are required.

Accordingly, an oral composition is demanded to be realized, which not only sufficiently inhibits a stain from adhering to the surface of teeth to enhance the whitening effect on teeth and the gloss-imparting effect on teeth, but also increases the amount of fluorine adsorption to teeth and decreases a feeling of astringency.

The present inventors have made various studies, and as a result, have found that when phytic acid and monofluorophosphoric acid are used in combination under specific conditions, provide is an oral composition which not only can unexpectedly promote adsorption of fluorine to teeth, but also can effectively prevent a stain from adhering to the surface of teeth, to favorably retain the whitening effect on teeth and to impart excellent gloss to teeth. Furthermore, the present inventors have also found that such an oral composition can effectively decrease a feeling of astringency derived from phytic acid and can also decrease a friction feeling, to provide a good feeling upon use.

The oral composition of the present invention not only can efficiently inhibit a colored stain from adhering to the surface of teeth to enhance the whitening effect on teeth and the gloss-imparting effect on teeth, but also can increase the amount of fluorine adsorption to teeth to allow fluorine to be efficiently incorporated into enamel or dentine, and can effectively reduce not only the feeling of astringency derived from phytic acid, but also the friction feeling, to ensure a good feeling upon use.

Hereinafter, the present invention is described in detail.

Herein, the feeling of astringency means a feeling caused when a tissue in the oral cavity, in particular, a mucosal tissue in the oral cavity (including tongue) such as gingiva is excessively shrunk, and is a feeling when roughness is felt around the mucosa in certain people. The friction feeling means a physical feeling of discomfort in teeth when an excess friction is felt upon contacting or rubbing teeth.

The oral composition of the present invention comprises, as a component (A), phytic acid or an alkali metal salt thereof in an amount of 0.04% by mass or more and 1% by mass or less in terms of phytic acid. While the phytic acid or the alkali metal salt thereof is known to be excellent in the removing effect on a minute stain adhering due to aging and the like and a stain such as tobacco tar, it can effectively inhibit additionally a stain from adhering to teeth in the present invention. Therefore, while the whitening effect on teeth can be sufficiently exerted, fluorine adsorption to teeth due to a monofluorophosphoric acid or an alkali metal salt thereof as a component (B) described later can also be efficiently promoted.

The phytic acid is also called another name: myo-inositol hexaphosphate; and is an inositol phosphate compound. Among various phosphate compounds, the phytic acid or the alkali metal salt thereof is particularly excellent in the gloss-imparting effect.

The alkali metal in the alkali metal salt as the component (A) includes sodium and potassium, and is preferably sodium in terms of taste and odor.

The content of the component (A) in the oral composition of the present invention is 0.04% by mass or more, preferably 0.1% by mass or more, more preferably 0.2% by mass or more in terms of phytic acid from the viewpoints of enhancing the suppressing effect on stain adhesion and efficiently promoting fluorine adsorption to teeth. The content of the component (A) in the oral composition of the present invention is 1% by mass or less, preferably 0.8% by mass or less, more preferably 0.7% by mass or less in terms of phytic acid from the viewpoints of not only further enhancing the suppressing effect on stain adhesion together with the monofluorophosphoric acid or the alkali metal salt thereof as the component (B), but also preventing the feeling of astringency and the friction feeling from being increased. In addition, the content of the component (A) is 0.04% by mass or more and 1% by mass or less, preferably from 0.1 to 0.8% by mass, more preferably from 0.2 to 0.7% by mass. The content of the phytic acid or the alkali metal salt thereof in the oral composition of the present invention, here adopted, is an amount in terms of phytic acid obtained by measuring the total amount by neutralization with potassium hydroxide or sodium hydroxide and converting it to an amount of the phytic acid.

The oral composition of the present invention comprises, as the component (B), monofluorophosphoric acid or the alkali metal salt thereof in an amount of 500 ppm or more and 1,500 ppm or less in terms of fluorine atoms. Inclusion of the component (B) in such an amount can increase the amount of fluorine adsorption to teeth and also retaining an excellent suppressing effect on stain adhesion, and can effectively decrease the feeling of astringency and the friction feeling derived from the component (A).

The alkali metal in the alkali metal salt as the component (B) includes sodium and potassium, and is preferably sodium.

The content of the component (B) in the oral composition of the present invention is 500 ppm or more, preferably 600 ppm or more, more preferably 800 ppm or more in terms of fluorine atoms from the viewpoints of allowing fluorine to favorably adsorb to teeth and effectively decreasing the feeling of astringency and the friction feeling. The content of the component (B) in the oral composition of the present invention is 1,500 ppm or less, preferably 1,200 ppm or less, more preferably 1,100 ppm or less in terms of fluorine atoms from the viewpoint of retaining a good suppressing effect on stain adhesion. In addition, the content of the component (B) in the oral composition of the present invention is 500 ppm or more and 1,500 ppm or less, preferably from 600 to 1,200 ppm, more preferably from 800 to 1,100 ppm in terms of fluorine atoms.

The mass ratio of the component (A) to the component (B), ((A)/(B)), is 0.1 or more, preferably 0.2 or more, more preferably 0.3 or more from the viewpoints of retaining an excellent suppressing effect on stain adhesion and also effectively promoting fluorine adsorption to teeth. The mass ratio of the component (A) to the component (B), ((A)/(B)), is 1.4 or less, preferably 1.2 or less, more preferably 1 or less, still more preferably 0.8 or less from the viewpoints of securing the amount of fluorine adsorption to teeth and also effectively decreasing the feeling of astringency and the friction feeling derived from the phytic acid. The mass ratio of the component (A) to the component (B), ((A)/(B)), is 0.1 or more and 1.4 or less, preferably from 0.2 to 1.2, more preferably from 0.3 to 1, still more preferably from 0.3 to 0.8.

The oral composition of the present invention does not comprise or comprises (F) a fluoride ion-supplying compound selected from the group consisting of sodium fluoride, potassium fluoride and ammonium fluoride in an amount of 100 ppm or less in terms of fluorine atoms. That is, while the oral composition of the present invention contains the component (B) in the specific amount mentioned above, the content of such a fluoride ion-supplying compound (F) is kept low because the fluoride ion-supplying compound may decrease the suppressing effect on stain adhesion and also impair the whitening effect and the gloss-imparting effect. The content of such a fluoride ion-supplying compound (F) in the oral composition of the present invention is 100 ppm or less, preferably 80 ppm or less, more preferably 50 ppm or less in terms of fluorine atoms from the viewpoint of efficiently preventing the suppressing effect on stain adhesion from being decreased, or the fluoride ion-supplying compound is not comprised except as unavoidably incorporated. Herein, while tin fluoride also supplies a fluoride ion like such a fluoride ion-supplying compound (F), the content of tin fluoride is restrained as a polyvalent metal cation because tin fluoride simultaneously supplies a polyvalent metal cation, from the viewpoints of preventing the suppressing effect on stain adhesion from being decreased and preventing the whitening effect and the gloss-imparting effect from being impaired.

The oral composition of the present invention does not comprise or comprises a polyvalent metal cation in an amount of less than 0.1-fold mol relative to the amount of the component (A) in terms of phytic acid. That is, in the oral composition of the present invention, the polyvalent metal cation causes the component (A) to be insoluble, decreases the suppressing effect on stain adhesion and also impairs the whitening effect and the gloss-imparting effect, and therefore the content thereof is kept low. The total content of the polyvalent metal cation is measured by ICP emission spectrometry (ICP emission spectrometer: Optima 5300DV manufactured by Perkin Elmer Inc.) and is less than 0.1-fold mol, preferably 0.02-fold mol or less relative to the amount of the component (A) in terms of phytic acid, or the polyvalent metal cation is not comprised except as unavoidably incorporated. Accordingly, an agent which supplies one or more polyvalent metal cations selected from the group consisting of aluminum, calcium, magnesium, iron, zinc, and tin is not desirably blended. Herein, a component including a polyvalent metal tends to release a polyvalent metal cation to decrease the effect of the present invention by the component (A), even if being, for example, an insoluble polyvalent metal salt and present in the composition in the form of a powder. Even an abrasive powder such as aluminum hydroxide supplies an aluminum ion to water present in the oral composition. Accordingly, it is considered that, when the oral composition of the present invention contains a polyvalent metal salt, a small amount of a cation is supplied to water included in the oral composition and/or the stain removal performance of the component (A) is deteriorated because the component (A) is adsorbed by contact of the polyvalent metal salt with the component (A).

In the oral composition of the present invention, a polyvalent cation other than the polyvalent metal cation, that is a polyvalent cation of a metal other than polyvalent metals of a cationic surfactant, a cationic antimicrobial agent and the like, and an adsorbent such as zeolite and activated carbon may cause the component (A) to be insoluble, possibly resulting in a decrease in the suppressing effect on stain adhesion or decreases in the whitening effect and the gloss-imparting effect. Accordingly, the total content of one or more polyvalent cations of a metal other than polyvalent metals of a cationic antimicrobial agent and the like, selected therefrom, and the adsorbent such as zeolite and activated carbon in the oral composition of the present invention is preferably less than 0.001% by mass, more preferably 0.0001% by mass or less from the viewpoint of inhibiting the suppressing effect on colored stain adhesion from being decreased, and the polyvalent cations of a metal other than polyvalent metals of a cationic antimicrobial agent and the like, and the adsorbent such as zeolite and activated carbon are not preferably contained except as unavoidably incorporated.

The oral composition of the present invention does not comprise or comprises polyphosphoric acid or a salt thereof in an amount of 20% by mass or less in terms of acid relative to the amount of the component (A) in terms of phytic acid. Such polyphosphoric acid or a salt thereof may decrease the effect of fluorine adsorption to teeth in an environment where the component (B) is present, as in the oral composition of the present invention, and therefore the content thereof in the oral composition of the present invention is restrained. The polyphosphoric acid or the salt thereof includes one or more selected from the group consisting of pyrophosphoric acid, tripolyphosphoric acid, hexametaphosphoric acid, and salts thereof. The content of the polyphosphoric acid or the salt thereof in the oral composition of the present invention is 20% by mass or less, preferably 10% by mass or less, more preferably 8% by mass or less and is preferably more than 0% by mass in terms of acid relative to the amount of the component (A) in terms of phytic acid from the viewpoint of efficiently preventing the effect of fluorine adsorption to teeth derived from the component (B) from being decreased, or the polyphosphoric acid or the salt thereof is not contained except as unavoidably incorporated.

When the oral composition of the present invention is a dentifrice composition, preferably a toothpaste composition, it preferably further contains a binder (C) from the viewpoints of enhancing storage stability, ensuring proper shape retainability and also favorably diffusing the oral composition of the present invention in the oral cavity. Such a binder includes one or more selected from the group consisting of sodium alginate, sodium carboxymethylcellulose, carrageenan, xanthan gum, sodium polyacrylate, hydroxyethylcellulose, hydroxypropylcellulose, pectin, tragacanth gum, gum arabic, guar gum, karaya gum, locust bean gum, gellan gum, tamarind gum, psyllium seed gum, polyvinyl alcohol, sodium chondroitin sulfate, and a methoxyethylene-maleic anhydride copolymer. Among them, the binder is preferably one or more, more preferably two or more selected from the group consisting of sodium carboxymethylcellulose having a degree of etherification of from 0.7 to 2.0, carrageenan and xanthan gum. The content of the component (C) in the dentifrice composition of the present invention is preferably 0.1% by mass or more, more preferably 0.2% by mass or more and preferably 2% by mass or less, more preferably 1.5% by mass or less.

The oral composition of the present invention can contain a thickening silica having an amount of oil absorption of from 150 to 500 mL/100 g together with the component (C). The thickening silica is larger in the amount of oil absorption than a silica which is commonly blended as an abrasive silica in a dentifrice. The amount of oil absorption of such thickening silica is preferably from 200 to 400 mL/100 g, more preferably from 250 to 380 mL/100 g from the viewpoints of ensuring storage stability by the binder, also ensuring proper shape retainability, and diffusing the oral composition of the present invention favorably in the oral cavity. As the thickening silica, a commercial product such as SYLOPURE 25 produced by Fuji Silysia Chemical Ltd. or SORBOSIL TC 15 produced by CROSFIELD Inc. can be used. Herein, the amount of oil absorption is measured through the amount of boiled linseed oil to be absorbed, according to JIS K5101-13-2 (established in 2004). In addition, the average particle size of the thickening silica to be used is preferably from 1 to 10 μm, more preferably from 1.5 to 8 μm, even more preferably from 2 to 8 μm.

The content of the thickening silica in the oral composition of the present invention is preferably more than 0% by mass, more preferably 2% by mass or more, and preferably 10% by mass or less, more preferably 8% by mass or less from the viewpoints of ensuring storage stability by the binder, also ensuring proper shape retainability to be ensured, and diffusing the oral composition of the present invention favorably in the oral cavity.

The oral composition of the present invention preferably contains glycerin (D) whose content is kept low, from the viewpoints of ensuring proper moisture-retaining property and also ensuring good dissolution or dispersion of each component in the composition, and the viewpoint of not inhibiting promotion of fluorine adsorption to teeth. When the oral composition of the present invention is a dentifrice composition, the content of such a component (D) in the dentifrice composition of the present invention is preferably 25% by mass or less, more preferably 20% by mass or less and is preferably 3% by mass or more, more preferably 5% by mass or more. When the oral composition of the present invention is a liquid oral composition, the content of the component (D) in the liquid oral composition of the present invention is preferably 15% by mass or less, more preferably 10% by mass or less and is preferably 1% by mass or more, more preferably 2% by mass or more.

When the oral composition of the present invention is a dentifrice composition, it preferably contains more than 0% by mass and 50% by mass or less of a sugar alcohol (E-1)

having a solubility in water at 20° C. of less than 40% by mass, and/or preferably contains 10% by mass or more and 35% by mass or less of a sugar alcohol (E-2) having a solubility in water at 20° C. of 40% by mass or more, from the viewpoints of enhancing effectiveness of the decreasing effect on the feeling of astringency, the friction feeling and the like, and enhancing the gloss-imparting effect. When containing the sugar alcohol (E-1), the oral composition of the present invention preferably contains two sugar alcohols different in the solubility in water: the component (E-1) and the component (E-2); in specific amounts.

The sugar alcohol as the component (E-1) has a solubility in water at 20° C. of less than 40% by mass (less than 40 g of the component (E-1) is soluble in 100 g of a saturated aqueous solution at 20° C.), and such a component (E-1) includes one or more selected from the group consisting of erythritol (solubility in water: 33% by mass), reduced palatinose which is a mixture of α-D-glucopyranosyl-1,6-sorbitol and α-D-glucopyranosyl-1,6-mannitol (solubility in water: 28% by mass), mannitol (solubility in water: 18% by mass), and glucopyranosyl sorbitol which is α-D-glucopyranosyl-1,6-sorbitol or α-D-glucopyranosyl-1,6-mannitol. Such a component (E-1) is preferably one or two selected from the group consisting of erythritol and reduced palatinose from the viewpoint of imparting favorable structural viscosity to the composition, more preferably erythritol from the viewpoint of providing a more excellent feeling upon use.

The content of the component (E-1) in the oral composition of the present invention is preferably more than 0% by mass, more preferably 20% by mass or more, and preferably 50% by mass or less, more preferably 45% by mass or less. In addition, the content of the component (E-1) in the oral composition of the present invention is preferably more than 0% by mass and 50% by mass or less, more preferably from 20 to 45% by mass.

The sugar alcohol as the component (E-2) has a solubility in water at 20° C. of 40% by mass or more (40 g or more of the component (E-2) is soluble in 100 g of a saturated aqueous solution at 20° C.), and such a component (E-2) includes one or more selected from the group consisting of xylitol (solubility in water at 20° C.: 66% by mass), maltitol (solubility in water at 20° C.: 60% by mass) and sorbitol (solubility in water at 20° C.: 72% by mass). Such a component (E-2) is preferably sorbitol from the viewpoint of ensuring a good feeling upon use.

The content of the component (E-2) in the oral composition of the present invention is preferably 10% by mass or more, more preferably 15% by mass or more, and preferably 35% by mass or less, more preferably 30% by mass or less. In addition, the content of the component (E-2) in the oral composition of the present invention is preferably from 10 to 35% by mass, more preferably from 15 to 30% by mass.

The total content of the component (E-1) and the component (E-2) in the oral composition of the present invention is preferably 15% by mass or more, more preferably 25% by mass or more, and preferably 70% by mass or less, more preferably 65% by mass or less from the viewpoints of ensuring a good feeling upon use, imparting a proper viscosity and forming a proper structure, suppressing the friction feeling, and enhancing the gloss-imparting effect on teeth.

From the viewpoint that the oral composition of the present invention allows the surface of teeth to be smooth to thereby provide luster to teeth, namely, achieve the effect of imparting natural gloss to teeth, the content of a hydrogen peroxide source in the oral composition of the present invention is preferably 0.1% by mass or less, more preferably 0.01% by mass or less, even more preferably 0.001% by mass or less and is preferably more than 0% by mass, or a hydrogen peroxide source is not preferably contained except as unavoidably incorporated. Such a hydrogen peroxide source is a component which generates hydrogen peroxide in the oral composition, and specifically includes hydrogen peroxide, urea peroxide, calcium peroxide, percarbonate such as sodium percarbonate, peroxyacid, persulfate such as sodium persulfate, sodium percarbonate, a crosslinked polyvinylpyrrolidone-hydrogen peroxide complex, and sodium perborate.

The oral composition of the present invention, even when being a dentifrice composition, can effectively decrease the feeling of astringency derived from phytic acid and the friction feeling, as described above, and therefore can keep the content of an organic resin powder low. Examples of such an organic resin powder include a polyolefin powder such as a polyethylene powder and a polypropylene powder; a polyamide powder including a nylon powder; an acrylic powder, a fluororesin powder, an ABS (acrylonitrile-butadiene-styrene copolymer) resin powder, an epoxy resin powder, an FRP (fiber-reinforced plastic) resin powder, and a vinyl chloride resin powder. The content of such an organic resin powder in the dentifrice composition of the present invention is preferably 2% by mass or less, more preferably 1% by mass or less, even more preferably 0.1% by mass or less from the viewpoint of avoiding a rough feeling from remaining in the oral cavity and the viewpoint of the feeling upon use, or the organic resin powder may not be contained except as unavoidably incorporated.

When the oral composition of the present invention is a dentifrice composition, it can exert an excellent suppressing effect on stain adhesion and also have a good feeling upon use with the feeling of astringency and the friction feeling being decreased, as described above, to thereby keep the content of an abrasive low. Such an abrasive is preferably an abrasive other than a polyvalent metal cation-containing abrasive, such as calcium phosphate, calcium hydrogen phosphate, calcium carbonate, aluminum hydroxide, aluminum silicate or zirconium silicate, more preferably abrasive silica (having 50 to 150 mL/100 g of the amount of oil absorption measured through the amount of boiled linseed oil to be absorbed, according to JIS K5101-13-2 (established in 2004)) or the like. The RDA value of the abrasive, (Radioactive Dentine Abrasion values, measured by the abradability test method according to ISO 11609 (Protocol A)), is generally from 20 to 250. The content of the abrasive other than a polyvalent metal cation-containing abrasive, in the oral composition of the present invention, is preferably 20% by mass or less, more preferably 10% by mass or less and is preferably 1% by mass or more, more preferably 2% by mass or more. Herein, since calcium phosphate, calcium hydrogen phosphate, calcium carbonate, aluminum hydroxide, aluminum silicate and zirconium silicate are polyvalent metal cation-containing abrasives, and therefore decrease the suppressing effect on stain adhesion and the gloss-imparting effect on teeth due to the component (A). The content of such a polyvalent metal cation-containing abrasive, in the dentifrice composition of the present invention, is preferably 1% by mass or less, more preferably 0.5% by mass or less, and the polyvalent metal cation-containing abrasive is not preferably contained except as unavoidably incorporated.

The oral composition of the present invention contains water in addition to the above components. The water in the present invention means all water included in the oral composition, including not only purified water and the like blended in the oral composition, but also water included in the respective components blended, such as 70% sorbitol liquid (aqueous sorbitol solution) used in formulation. Inclusion of such water can ensure a good shape retainability and also dissolve or disperse the respective components in the composition favorably to thereby diffuse the components in the oral cavity, exerting a desired effect sufficiently. When the oral composition is a dentifrice composition, the content of the water in the dentifrice composition of the present invention is preferably 10% by mass or more, more preferably 12% by mass or more and is preferably 50% by mass or less, more preferably 40% by mass or less. When the oral composition of the present invention is a liquid oral composition, the content of the water in the liquid oral composition of the present invention is preferably 60% by mass or more, more preferably 70% by mass or more, even more preferably 80% by mass or more and is preferably 99.5% by mass or less, more preferably 99% by mass or less.

Herein, while the content of the water in the oral composition of the present invention can be calculated from the amount of water blended and the amount of water in the components blended, it can be measured by, for example, a Karl-Fischer moisture meter. As the Karl-Fischer moisture meter, for example, a trace moisture analyzer (Hiranuma Sangyo Corporation) can be used. In this analyzer, the amount of water can be measured by taking 5 g of the oral composition, suspending it in 25 g of anhydrous methanol, and fractionating 0.02 g of this suspension.

The pH of the oral composition of the present invention is from 5.5 to 6.5. That is, when the oral composition of the present invention is applied into the oral cavity, the pH of the oral composition of the present invention is 5.5 or more, preferably 5.8 or more and is 6.5 or less, preferably 6.2 or less, from the viewpoint of exerting the suppressing effect of the component (A) on adhesion of stain due to drinking and eating to enhance the whitening effect on teeth and the gloss-imparting effect on teeth.

When the oral composition of the present invention is a dentifrice composition, the pH cannot be accurately measured in the case of a dentifrice composition having a high viscosity, such as a toothpaste, and therefore the pH of the dentifrice composition of the present invention is defined as a pH of a dilution obtained by diluting the composition with water to 10% by mass. Thus, regarding the pH value of the dentifrice composition of the present invention, dilution with saliva when applied into the oral cavity, namely, dilution due to such use in the oral cavity is also assumed.

Herein, the pH of the oral composition of the present invention is a value measured by use of a pH electrode at 25° C., and means a value measured without dilution when the oral composition of the present invention is a liquid oral composition, and means a value measured after addition of distilled water for adjustment of the concentration of the dentifrice composition to obtain 10% by mass of the aqueous solution, as described above, when the oral composition of the present invention is a dentifrice composition.

A pH adjuster is preferably used in order to adjust the pH of the oral composition of the present invention to the above range. Such a pH adjuster includes one or more selected from the group consisting of salts of organic acids such as acetic acid, fumaric acid, malic acid, lactic acid, gluconic acid and tartaric acid, salts of inorganic acids such as phosphoric acid (for example, orthophosphoric acid) other than phytic acid, hydrochloric acid and sulfuric acid, hydroxides such as sodium hydroxide and potassium hydroxide, ammonia or ammonia water, lower alkanolamines, and basic amino acids such as arginine and lysine, as long as the stain removing effect of phytic acid is not impaired. Such a pH adjuster is preferably one or more selected from the group consisting of organic acids other than phytic acid, inorganic acids other than pyrophosphoric acid, and basic amino acids. The content of any organic acid and any inorganic acid (excluding phytic acid and pyrophosphoric acid) among the above pH adjusters is preferably 5% by mass or less, more preferably 1% by mass or less relative to the amount of the component (A) in terms of phytic acid, from the viewpoint of not inhibiting the effects of phytic acid and sodium monofluorophosphate.

When the oral composition of the present invention is a dentifrice composition, the viscosity at 25° C. is preferably from 1,000 to 4,000 dPa·s, more preferably from 1,500 to 3,500 dPa·s from the viewpoint of favorably providing both of shape retainability and the feeling upon use.

Herein, the viscosity at 25° C. of the dentifrice composition of the present invention can be measured by packing the dentifrice composition in a viscosity measurement vessel and storing the resultant in a thermostat at 25° C. for 24 hours, and thereafter using a Helipath viscometer (TVB-10R manufactured by Toki Sangyo Co., Ltd.) in conditions of a rotor T-C, a number of rotations of 2.5 rpm and 1 minute.

The oral composition of the present invention can further contain a surfactant such as an anionic surfactant and a nonionic surfactant; a wetting agent other than glycerin and a sugar alcohol; a flavor; a dye; a nonionic bactericidal agent such as triclosan and isopropylmethylphenol; and other active component, as long as the effect of the present invention is not impaired.

Herein, nitrate such as potassium nitrate is preferably limited with respect to the content thereof from the viewpoint of retaining a good taste. Specifically, the content of nitrate such as potassium nitrate in the oral composition of the present invention is preferably less than 0.1% by mass, more preferably 0.05% by mass or less, even more preferably 0.01% by mass or less, or such nitrate is not preferably contained except as unavoidably incorporated.

The oral composition of the present invention can be appropriately used as a dentifrice composition such as a toothpaste composition or a powder dentifrice, or as a liquid oral composition such as mouthwash or a liquid dentifrice, depending on the intended use.

When the oral composition of the present invention is a liquid oral composition, it can be used by holding 5 to 30 mL of the composition in the oral cavity per one-time use, gargling it, and thereafter discharging it from the mouth, and when the oral composition of the present invention is a dentifrice composition, it can be used by taking 1 g to 10 g, preferably 1 g to 5 g of the composition on a toothbrush, and brushing teeth together with the composition by use of the toothbrush. Such use can allow for selective adsorption of fluorine while a colored stain is inhibited from adhering. In addition, when the fluoride ion-supplying compound (F) such as sodium fluoride is present in an oral composition, the whitening effect of phytic acid on teeth and the glossing effect of phytic acid on teeth may be decreased. The oral composition of the present invention, however, can inhibit impairment of the effect of the phytic acid or the salt thereof (A), to allow fluorine derived from the component (B) to adsorb to teeth.

With respect to the above embodiments, the present invention further discloses the following oral compositions.

[1] An oral composition comprising the following components (A) and (B):
(A) phytic acid or an alkali metal salt thereof in an amount of 0.04% by mass or more and 1% by mass or less in terms of phytic acid; and
(B) monofluorophosphoric acid or an alkali metal salt thereof in an amount of 500 ppm or more and 1500 ppm or less in terms of fluorine atoms, wherein
the mass ratio of the component (A) to the component (B), ((A)/(B)), is 0.1 or more and 1.4 or less,
wherein the composition does not comprise or comprises a fluoride ion-supplying compound (F) selected from the group consisting of sodium fluoride, potassium fluoride and ammonium fluoride in an amount of 100 ppm or less in terms of fluorine atoms,
the composition does not comprise or comprises a polyvalent metal cation in an amount of less than 0.1-fold mol relative to the component (A), the composition does not comprise or comprises polyphosphoric acid or a salt thereof in an amount of 20% by mass or less in terms of acid relative to the component (A), and the pH thereof is from 5.5 to 6.5.

[2] The oral composition according to [1], wherein the content of the component (A) is preferably 0.1% by mass or more, more preferably 0.2% by mass or more and is preferably 0.8% by mass or less, more preferably 0.7% by mass or less in terms of phytic acid.

[3] The oral composition according to [1] or [2], wherein the content of the component (B) is preferably 600 ppm or more, more preferably 800 ppm or more, and preferably 1,200 ppm or less, more preferably 1,100 ppm or less in terms of fluorine atoms.

[4] The oral composition according to any one of [1] to [3], wherein the mass ratio of the component (A) to the component (B), ((A)/(B)), is preferably 0.2 or more, more preferably 0.3 or more and is preferably 1.2 or less, more preferably 1 or less, even more preferably 0.8 or less.

[5] The oral composition according to any one of [1] to [4], wherein the component (A) is preferably phytic acid or a sodium salt thereof, and the component (B) is preferably monofluorophosphoric acid or a sodium salt thereof.

[6] The oral composition according to any one of [1] to [5], wherein the content of the fluoride ion-supplying compound (F) is preferably 80 ppm or less, more preferably 50 ppm or less in terms of fluorine atoms, or the fluoride ion-supplying compound is not comprised.

[7] The oral composition according to any one of [1] to [6], wherein the total content of the polyvalent metal cation is preferably 0.02-fold mol or less relative to the amount of the component (A) in terms of phytic acid, or the polyvalent metal cation is not comprised.

[8] The oral composition according to any one of [1] to [7], wherein the polyvalent metal cation is one or more selected from the group consisting of aluminum, calcium, magnesium, iron, zinc and tin.

[9] The oral composition according to any one of [1] to [8], wherein the content of a polyvalent metal cation-comprising abrasive is preferably 1% by mass or less.

[10] The oral composition according to any one of [1] to [9], wherein the polyphosphoric acid or the salt thereof is preferably one or more selected from the group consisting of pyrophosphoric acid, tripolyphosphoric acid, hexametaphosphoric acid or salts thereof.

[11] The oral composition according to any one of [1] to [10], wherein the content of the polyphosphoric acid or the salt thereof is preferably 10% by mass or less, more preferably 8% by mass or less and is preferably more than 0% by mass in terms of acid relative to the amount of the component (A) in terms of phytic acid, or the polyphosphoric acid or the salt thereof is not comprised.

[12] The oral composition according to any one of [1] to [11], wherein the composition is preferably a dentifrice composition and further comprises a binder (C), and the content of the component (C) is preferably 0.1% by mass or more, more preferably 0.2% by mass or more and is preferably 2% by mass or less, more preferably 1.5% by mass or less.

[13] The oral composition according to any one of [1] to [12], wherein the content of a glycerin (D) is preferably 25% by mass or less, more preferably 20% by mass or less and is preferably 3% by mass or more, more preferably 5% by mass or more.

[14] The oral composition according to any one of [1] to [13], wherein the composition preferably comprises more than 0% by mass and 50% by mass or less of a sugar alcohol (E-1) having a solubility in water at 20° C. of less than 40% by mass, and/or preferably comprises 10% by mass or more and 35% by mass or less of a sugar alcohol (E-2) having a solubility in water at 20° C. of 40% by mass or more.

[15] The oral composition according to [14], wherein the component (E-1) is preferably one or two selected from the group consisting of erythritol and reduced palatinose, more preferably erythritol.

[16] The oral composition according to [14] or [15], wherein the component (E-2) is preferably sorbitol.

[17] The oral composition according to any one of [14] to [16], wherein the content of the component (E-1) is more preferably 20% by mass or more and is more preferably 45% by mass or less.

[18] The oral composition according to any one of [14] to [17], wherein the content of the component (E-2) is more preferably 15% by mass or more and is more preferably 30% by mass or less.

[19] The oral composition according to any one of [14] to [18], wherein the total content of the component (E-1) and component (E-2) is preferably 15% by mass or more, more preferably 25% by mass or more and is preferably 70% by mass or less, more preferably 65% by mass or less.

[20] The oral composition according to any one of [1] to [19], wherein the content of a hydrogen peroxide source is preferably 0.01% by mass or less, more preferably 0.001% by mass or less, even more preferably 0.0001% by mass or less and is preferably more than 0% by mass, or the hydrogen peroxide source is not preferably comprised.

[21] The oral composition according to [20], wherein the hydrogen peroxide source is selected from the group consisting of hydrogen peroxide, urea peroxide, calcium peroxide, percarbonate, peroxyacid, persulfate, sodium percarbonate, a crosslinked polyvinylpyrrolidone-hydrogen peroxide complex and sodium perborate, and the content of the hydrogen peroxide source is the total amount thereof.

[22] The oral composition according to any one of [1] to [21], wherein the content of an organic resin powder is preferably 2% by mass or less, more preferably 1% by mass or less, even more preferably 0.1% by mass or less, or an organic resin powder is not comprised.

[23] The oral composition according to any one of [1] to [22], wherein the composition is preferably a dentifrice composition and preferably comprises an abrasive other than a polyvalent metal cation-comprising abrasive, and the content of the abrasive is preferably 20% by mass or less, more preferably 10% by mass or less and is preferably 1% by mass or more, more preferably 2% by mass or more.

[24] The oral composition according to any one of [1] to [23], wherein the composition is preferably a dentifrice composition, and the content of water is preferably 10% by mass or more, more preferably 12% by mass or more and is preferably 50% by mass or less, more preferably 40% by mass or less.

[25] The oral composition according to any one of [1] to [24], wherein the composition is preferably a liquid oral composition, and the content of water is preferably 60% by mass or more, more preferably 70% by mass or more, even more preferably 80% by mass or more and is preferably 99.5% by mass or less, more preferably 99% by mass or less.

[26] The oral composition according to any one of [1] to [25], wherein the composition is preferably a dentifrice composition, and the pH at 25° C. when diluted with water to 10% by mass is preferably 5.8 or more and is preferably 6.2 or less.

[27] The oral composition according to any one of [1] to [26], wherein the composition is preferably a dentifrice composition, and the viscosity at 25° C. is preferably from 1,000 to 4,000 dPa·s, more preferably from 1,500 to 3,500 dPa·s.

[28] The oral composition according to any one of [1] to [27], wherein the content of an adsorbent selected from the group consisting of zeolite and activated carbon is preferably less than 0.001% by mass, more preferably 0.0001% by mass or less, or an adsorbent selected from the group consisting of zeolite and activated carbon is not comprised.

[29] The oral composition according to any one of [1] to [28], wherein the composition is comprises a pH adjuster, the pH adjuster is preferably one or more selected from the group consisting of an organic acid other than phytic acid, or a salt thereof, an inorganic acid other than pyrophosphoric acid, or a salt thereof, and a basic amino acid, and the content of the pH adjuster is preferably 5% by mass or less, more preferably 1% by mass or less relative to the amount of the component (A) in terms of phytic acid.

[30] The oral composition according to any one of [1] to [29], wherein the content of potassium nitride is preferably less than 0.1% by mass, more preferably 0.05% by mass or less, even more preferably 0.01% by mass or less, or potassium nitride is not comprised.

[31] Use of the oral composition according to any one of [1] to [20], for adsorbing fluorine to teeth while inhibiting stain adhesion to teeth.

[32] Use of the oral composition according to any one of [1] to [30], for adsorbing fluorine to teeth while inhibiting stain adhesion to teeth and imparting gloss to teeth.

[33] Use of the oral composition according to any one of [1] to [30], for producing an agent for imparting gloss to teeth, the agent inhibiting stain adhesion to teeth and adsorbing fluorine to teeth.

EXAMPLES

Hereinafter, the present invention is specifically described based on Examples. Herein, the content of each component is represented by % by mass unless particularly stated in tables.

Examples 1 to 2 and Comparative Examples 1 to 2

Each dentifrice composition was prepared according to each formulation shown in Table 1. Next, evaluation of the feeling of astringency was performed according to the following method.

The results are shown in Table 1.

<<Evaluation of Feeling of Astringency>>

Ten subjects (male: 5, female: 5) took 1 g of each dentifrice composition on a toothbrush, and brushed their teeth freely for about 2 minutes. After rinsing of their mouths, the number of subjects who strongly felt the feeling of astringency was counted. It is indicated that, as such a value is smaller, the feeling of astringency is favorably reduced.

<<Evaluation of Friction Feeling>>

Ten subjects (male: 5, female: 5) took 1 g of each dentifrice composition on a toothbrush, and brushed their teeth freely for about 2 minutes. After rinsing of their mouths, the number of subjects who strongly felt friction was counted. It is indicated that, as such a value is smaller, no friction is felt and the composition is excellent in feeling upon use.

TABLE 1

|  |  | Example 1 | Example 2 | Comparative Example 1 | Comparative Example 2 |
|---|---|---|---|---|---|
| (A) | Phytic acid (50% aqueous solution) | 1.0 | 0.6 | 1.0 | 3.0 |
| (B) | Sodium monofluorophosphate | 0.72 | 0.72 | 0.00 | 0.72 |
|  | Erythritol |  | 40.0 |  |  |
|  | Sorbitol liquid (70% aqueous solution) | 38.58 | 28.10 | 38.60 | 38.58 |
|  | Sodium hydroxide liquid (48% aqueous solution) | 0.4 | 0.2 | 0.4 | 1.2 |
|  | Glycerin | 20.0 | 8.0 | 20.0 | 20.0 |
|  | Sodium lauryl sulfate | 1.5 | 1.5 | 1.5 | 1.5 |
|  | Sodium carboxymethylcellulose | 0.8 | 0.25 | 0.8 | 0.8 |
|  | Xanthan gum | 0.1 | 0.07 | 0.1 | 0.1 |
|  | Polyethylene glycol | 5.0 | 3.0 | 5.0 | 5.0 |
|  | Saccharin sodium | 0.10 | 0.06 | 0.10 | 0.10 |
|  | Thickening silica | 8.0 | 4.7 | 8.0 | 8.0 |
|  | Abrasive silica | 5.0 | 5.0 | 5.0 | 5.0 |
|  | Purified water | 17.80 | 6.80 | 18.50 | 15.00 |
|  | Flavor | 1.0 | 1.0 | 1.0 | 1.0 |
| Total |  | 100.00 | 100.00 | 100.00 | 100.00 |
| Amount of water |  | 30.1 | 15.6 | 30.8 | 28.7 |
| (A) (Amount in terms of phytic acid) |  | 0.5 | 0.3 | 0.5 | 1.5 |
| (A)/(B) |  | 0.69 | 0.42 | — | 2.08 |
| Viscosity (dPa · s) |  | 1808 | 2112 | 1744 | 1840 |
| pH |  | 6.3 | 6.3 | 6.4 | 6.2 |

TABLE 1-continued

|  | Example 1 | Example 2 | Comparative Example 1 | Comparative Example 2 |
|---|---|---|---|---|
| Feeling of astringency (number of subject(s)) | 3 | 0 | 6 | 5 |
| Friction feeling (number of subject(s)) | 1 | 1 | 3 | 5 |

It is found from the results in Table 1 that the feeling of astringency and the friction feeling were effectively reduced in each of Example 1 and Example 2 as compared with Comparative Example 1 where no component (B) was contained and Comparative Example 2 where the (A)/(B) was not within the above range.

Examples 3 to 4 and Comparative Examples 3 to 5

Each liquid oral composition, which was for measurement of the amount of fluorine adsorption, was prepared according to each formulation shown in Table 2. Next, the amount of fluorine adsorption was measured and evaluated according to the following method.

The results are shown in Table 2 and FIG. 1.

<<Evaluation of Amount of Fluorine Adsorption>>

After a HAP pellet (hydroxyapatite pellet) was immersed in each liquid oral composition five times for every 3 minutes, the HAP pellet was washed with water and dried. Next, the HAP pellet was treated with 1 N hydrochloric acid for 1 minute to extract fluorine adsorbed, and the amount of fluorine adsorption was then quantitatively determined with an ion analyzer (Expandable ion Analyzer EA940 (manufactured by ORION Corporation)) by use of a fluoride ion electrode (ionplus-Fluoride (manufactured by ORION Corporation)). The operation was repeated five times, and the average of the values obtained by quantitative determination was determined and defined as an index of evaluation of the amount of fluorine adsorption. Table 2 further shows the increase rate (%) in the amount of fluorine adsorption under assumption of the amount of fluorine adsorption in Comparative Example 4 being 100%.

amount of fluorine adsorption to teeth in Comparative Example 5 where sodium pyrophosphate was further contained in an amount of more than 20% by mass in terms of acid relative to the component (A) was decreased.

Examples 5 to 6 and Comparative Examples 6 to 8

Each liquid oral composition, for evaluation of the suppressing effect on adhesion of stain to teeth, was prepared according to each formulation shown in Table 3. Next, the suppressing effect on adhesion of colored stain of tea was evaluated according to the following method.

The results are shown in Table 3.

<<Evaluation of Suppressing Effect on Stain Adhesion>>

After a HAP pellet for use in the test was abraded by using abrasive paper (#1200), it was subjected to ultrasonic cleaning for 1 minute. Next, the resulting HAP pellet was immersed in each test liquid for 3 minutes, thereafter washed with water for 30 seconds, then immersed in a 1% bovine serum albumin solution and a black tea solution, in this order, for every 3 minutes, and then dried. After the operation was repeated ten times, the value of $b^*$ in representing of the degree of stain by using the $L^*a^*b$ color system (Munsell color system) was measured by use of a spectral colorimeter (CM-700d, manufactured by Konica Minolta, Inc.) to determine the value of $\Delta b^*$ which was the difference from the value of $b^*$ before immersion.

Herein, the value of $b^*$ of the HAP pellet which was immersed in water for 3 minutes instead of the test liquid in Comparative Example 6 was also measured in the same manner to determine the $\Delta b^*$. It is meant that, as the $\Delta b^*$ is smaller, namely, the absolute value of $\Delta b^*$ is larger, adhesion of stain is efficiently suppressed and whitening of teeth is retained.

TABLE 2

|  |  | Comparative Example 3 | Comparative Example 4 | Example 3 | Example 4 | Comparative Example 5 |
|---|---|---|---|---|---|---|
| (A) | Phytic acid | 0.0 | 0.0 | 0.3 | 0.5 | 0.3 |
| (B) | Sodium monofluorophosphate | 0.15 | 0.72 | 0.72 | 0.72 | 0.72 |
|  | Sodium pyrophosphate | 0.0 | 0.0 | 0.0 | 0.0 | 0.4 |
|  | pH Adjuster (adjustment to pH = 6) | q.s. | q.s. | q.s. | q.s. | q.s. |
|  | Purified water | Balance | Balance | Balance | Balance | Balance |
| Total |  | 100.0 | 100.0 | 100.0 | 100.0 | 100.0 |
| (B) (Amount in terms of fluorine atoms (ppm)) |  | 200 | 1000 | 1000 | 1000 | 1000 |
| (A)/(B) |  | — | — | 0.42 | 0.69 | 0.42 |
| Increase rate in amount of fluorine adsorption (%) |  | 63 | 100 | 112 | 109 | 85 |
| Amount of fluorine adsorption ($\mu g/cm^2$) |  | 0.0453 | 0.0716 | 0.0799 | 0.0781 | 0.0611 |

Figure 2:
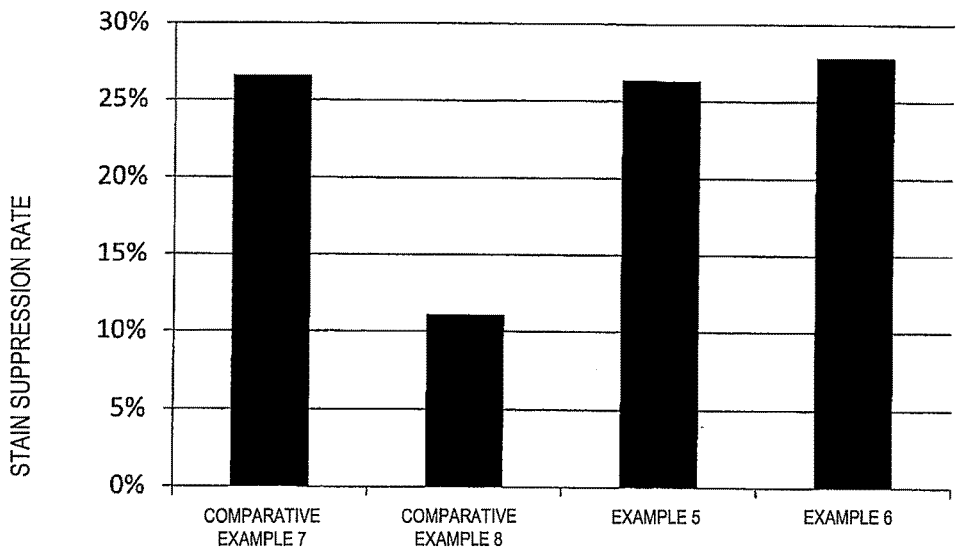
FIG. 2 is a graph illustrating a staining suppression rate in each of Examples 5 to 6 and Comparative Example 7 to 8 relative to Comparative Example 6.

It is found from the results in Table 2 and FIG. 1 that while the amount of fluorine adsorption to teeth in each of Examples 3 to 4 where the component (A) was contained was increased as compared with that in Comparative Example 4 where no component (A) was contained, the The results are shown in Table 3 and FIG. 2. Table 3 shows the absolute value of $\Delta b^*$, and also shows the stain suppression rate (%) relative to that in Comparative Example 6 where water was used.

TABLE 3

|  |  | Comparative Example 6 | Comparative Example 7 | Comparative Example 8 | Example 5 | Example 6 |
|---|---|---|---|---|---|---|
| (A) | Phytic acid | 0 | 0.3 | 0.3 | 0.3 | 0.5 |
| (B) | Sodium monofluorophosphate | 0 | 0 | 0 | 0.72 | 0.72 |
|  | Sodium fluoride | 0 | 0 | 0.21 | 0 | 0 |
|  | Sodium pyrophosphate | 0 | 0 | 0 | 0 | 0 |
|  | pH Adjuster (adjustment to pH = 6) | q.s. | q.s. | q.s. | q.s. | q.s. |
|  | Purified water | 100.0 | Balance | Balance | Balance | Balance |
| Total |  | 100.0 | 100.0 | 100.0 | 100.0 | 100.0 |
| (B) (Amount in terms of fluorine atoms (ppm)) |  | 0 | 0 | 0 | 1000 | 1000 |
| Sodium fluoride (amount in terms of fluorine atoms) (ppm) |  | 0 | 0 | 1000 | 0 | 0 |
| (A)/(B) |  | — | — | — | 0.42 | 0.69 |
| Stain suppression rate (%) |  | 0.0 | 26.6 | 11.1 | 26.4 | 27.8 |
| Black tea stain (Δb*) |  | 10.74 | 7.88 | 9.55 | 7.91 | 7.75 |

It is found from the results in Table 3 and FIG. 2 that the suppressing effect on stain adhesion in each of Examples 5 to 6 was higher than that in Comparative Example 8 where sodium fluoride was contained, and was at the same level as that in Comparative Example 7 where the component (A) was contained, and therefore the suppressing effect on colored stain adhesion due to the component (A) could be maintained in each of Examples 5 to 6 while the component (B) was contained and the effect of fluorine adsorption to teeth was exerted.

Examples 7 to 14 and Comparative Examples 9 to 12

Each dentifrice composition was prepared according to each formulation shown in Table 4. Next, the friction feeling and the feeling of astringency were evaluated according to the following methods.

<<Evaluation of Friction Feeling and Feeling of Astringency>>

Three subjects (male: 2, female: 1) took 1 g of each dentifrice composition on a toothbrush, and brushed their teeth freely for about 2 minutes. After rinsing of their mouths, the friction feeling and the feeling of astringency were evaluated according to the following criteria. The results based on discussion among the subjects are shown in Table 4.

<Friction Feeling>
1: No friction was felt
2: Friction was slightly felt
3: Friction was felt
4: Friction was significantly felt <Feeling of Astringency>
1: No feeling of astringency
2: Slight feeling of astringency
3: Feeling of astringency
4: Significant feeling of astringency For each dentifrice composition shown in Table 4, a composition where the thickening silica and the abrasive silica were replaced with purified water was prepared, and subjected to <<Evaluation of amount of fluorine adsorption>> in the same manner as in the liquid oral composition in each of Examples 4 and 5 and subjected to <<Evaluation of suppressing effect on stain adhesion>> in the same manner as in the liquid oral composition in each of Examples 5 and 6.

The results are shown in Table 4.

TABLE 4

|  |  | Example 7 | Example 8 | Example 9 | Example 10 | Example 11 | Example 12 |
|---|---|---|---|---|---|---|---|
| (A) | Phytic acid (50% aqueous solution) | 0.3 | 0.6 | 1.6 | 0.6 | 0.6 | 0.6 |
| (B) | Sodium monofluorophosphate | 0.72 | 0.72 | 0.72 | 0.72 | 0.72 | 1.08 |
|  | Sodium anhydrous pyrophosphate (*1) | 0.02 | 0.02 | 0.02 | 0.04 | 0.02 | 0.02 |
|  | Sodium dihydrogen pyrophosphate |  |  |  |  |  |  |
|  | Zinc oxide |  |  |  |  | 0.0006 |  |
|  | Sodium hydroxide liquid (48% aqueous solution) | Adjusted | Adjusted | Adjusted | Adjusted | Adjusted | Adjusted |
| (D) | Glycerin | 8 | 8 | 8 | 8 | 8 | 8 |
|  | Erythritol | 5 | 5 | 5 | 5 | 5 | 5 |
|  | Sorbitol liquid (70% aqueous solution) | 32 | 32 | 32 | 32 | 32 | 32 |
|  | Xylitol | 30 | 30 | 30 | 30 | 30 | 30 |
|  | Sodium lauryl sulfate | 1.5 | 1.5 | 1.5 | 1.5 | 1.5 | 1.5 |
| (C) | Sodium carboxymethylcellulose | 0.22 | 0.22 | 0.22 | 0.22 | 0.22 | 0.22 |
|  | Polyethylene glycol (PEG-600) | 3 | 3 | 3 | 3 | 3 | 3 |
|  | Thickening silica (*2) | 5.0 | 5.0 | 5.0 | 5.0 | 5.0 | 5.0 |
|  | Abrasive silica (*3) | 5.0 | 5.0 | 5.0 | 5.0 | 5.0 | 5.0 |
|  | Purified water | Balance | Balance | Balance | Balance | Balance | Balance |
|  | Flavor | 1.0 | 1.0 | 1.0 | 1.0 | 1.0 | 1.0 |
| Total |  | 100.0 | 100.0 | 100.0 | 100.0 | 100.0 | 100.0 |
| Amount of water |  | 18 | 17 | 16 | 17 | 17 | 17 |
| PH |  | 6.0 | 6.0 | 6.0 | 6.0 | 6.0 | 6.0 |
| (A) (Amount in terms of phytic acid) |  | 0.15 | 0.30 | 0.80 | 0.30 | 0.30 | 0.30 |
| (B) Amount in terms of fluorine atoms (ppm) |  | 1000 | 1000 | 1000 | 1000 | 1000 | 1500 |
| (A)/(B) |  | 0.208 | 0.417 | 1.111 | 0.417 | 0.417 | 0.278 |
| Pyrophosphoric acid (amount in terms of acid) |  | 0.013 | 0.013 | 0.013 | 0.027 | 0.013 | 0.013 |

TABLE 4-continued

| | | | | | | |
|---|---|---|---|---|---|---|
| Molar amount of polyvalent metal cation relative to (A), (-fold mol) | — | — | — | — | 0.016 | — |
| Amount in terms of acid (% by mass) of polyphosphoric acid or salt thereof relative to (A) (amount in terms of phytic acid) | 8.9 | 4.5 | 1.7 | 8.9 | 4.5 | 4.5 |
| Friction feeling | 2 | 1 | 1 | 2 | 1 | 2 |
| Feeling of astringency | 1 | 1 | 1 | 2 | 2 | 1 |
| Increase rate in amount of fluorine adsorption (%) | 103 | 110 | 108 | 107 | 109 | 107 |
| Amount of fluorine adsorption (µg/cm$^2$) | 0.0744 | 0.0794 | 0.0781 | 0.0776 | 0.0791 | 0.0776 |
| Black tea stain (Δb*) | 8.8 | 8.2 | 7.9 | 8.8 | 8.3 | 8.5 |

| | | Example 13 | Example 14 | Comparative Example 9 | Comparative Example 10 | Comparative Example 11 | Comparative Example 12 |
|---|---|---|---|---|---|---|---|
| (A) | Phytic acid (50% aqueous solution) | 0.6 | 0.6 | 0.0 | 0.6 | 0.6 | 0.6 |
| (B) | Sodium monofluorophosphate | 0.72 | 0.72 | 0.72 | 0.72 | 0 | 0.72 |
| | Sodium anhydrous pyrophosphate (*1) | 0.02 | 0.02 | | 0.40 | 0.02 | 0.02 |
| | Sodium dihydrogen pyrophosphate | | | 0.017 | | | |
| | Zinc oxide | | | | | | 0.01 |
| | Sodium hydroxide liquid (48% aqueous solution) | Adjusted | Adjusted | Adjusted | Adjusted | Adjusted | Adjusted |
| P) | Glycerin | 8 | 8 | 8 | 8 | 8 | 8 |
| | Erythritol | 5 | 5 | 5 | 5 | 5 | 5 |
| | Sorbitol liquid (70% aqueous solution) | 32 | 32 | 32 | 32 | 32 | 32 |
| | Xylitol | 30 | 30 | 30 | 30 | 30 | 30 |
| | Sodium lauryl sulfate | 1.5 | 1.5 | 1.5 | 1.5 | 1.5 | 1.5 |
| (C) | Sodium carboxymethylcellulose | 1.00 | 0.22 | 0.22 | 0.22 | 0.22 | 0.22 |
| | Polyethylene glycol (PEG-600) | 3 | 3 | 3 | 3 | 3 | 3 |
| | Thickening silica (*2) | 5.0 | 5.0 | 5.0 | 5.0 | 5.0 | 5.0 |
| | Abrasive silica (*3) | 5.0 | 5.0 | 5.0 | 5.0 | 5.0 | 5.0 |
| | Purified water | Balance | Balance | Balance | Balance | Balance | Balance |
| | Flavor | 1.0 | 1.0 | 1.0 | 1.0 | 1.0 | 1.0 |
| Total | | 100.0 | 100.0 | 100.0 | 100.0 | 100.0 | 100.0 |
| Amount of water | | 17 | 17 | 18 | 17 | 18 | 17 |
| PH | | 6.0 | 5.8 | 6.0 | 6.0 | 6.0 | 6.0 |
| (A) (Amount in terms of phytic add) | | 0.30 | 0.30 | 0.00 | 0.30 | 0.30 | 0.30 |
| (B)Amount in terms of fluorine atoms (ppm) | | 1000 | 1000 | 1000 | 1000 | 0 | 1000 |
| (A)/(B) | | 0.417 | 0.417 | 0.000 | 0.417 | — | 0.417 |
| Pyrophosphoric acid (amount in terms of add) | | 0.013 | 0.013 | 0.013 | 0.268 | 0.013 | 0.013 |
| Molar amount of polyvalent metal cation relative to (A), (-fold mol) | | — | — | — | — | — | 0.270 |
| Amount in terms of acid (% by mass) of polyphosphoric acid or salt thereof relative to (A) (amount in terms of phytic acid) | | 4.5 | 4.5 | — | 89.2 | 4.5 | 4.5 |
| Friction feeling | | 2 | 2 | 2 | 2 | 4 | 2 |
| Feeling of astringency | | 2 | 1 | 1 | 1 | 2 | 4 |
| Increase rate in amount of fluorine adsorption (%) | | 103 | 105 | 100 | 84 | 0 | 83 |
| Amount of fluorine adsorption (pig/cm$^2$) | | 0.0744 | 0.0763 | 0.0725 | 0.0608 | 0 | 0.0599 |
| Black tea stain (Δb*) | | 7.7 | 8.2 | 16.3 | 12 | 10.8 | 10.5 |

(*1): Tetrasodium pyrophosphate
(*2): SYLOPURE 25 (Fuji Silysia Chemical Ltd., amount of oil absorption 310 mL/100 g)
(*3): SORBOSIL AC77 (PQ Corporation, amount of oil absorption 129 mL/100 g)

Examples 8, 10, 11, 15, and Comparative Examples 10, 13

Each dentifrice composition was prepared according to each formulation shown in Table 5. Next, the friction feeling and the feeling of astringency were evaluated by three subjects in the same manner as the above method.

Furthermore, the gloss-imparting effect on human teeth was evaluated according to the following method, and the surfaces of human teeth were observed by SEM. In addition, a composition where thickening silica and abrasive silica were replaced with purified water was prepared, and subjected to <<Evaluation of suppressing effect on stain adhesion>> in the same manner as in the liquid oral composition in each of Examples 5 and 6. Furthermore, the gloss-imparting effect and the whitening effect were evaluated according to the following methods.

The results are shown in Table 5.
<<Evaluation of Gloss-Imparting Effect>>
(Treatment Method of Teeth Extracted)

The tests with respect to the gloss-imparting effect and the whitening effect described later were performed by use of human teeth extracted. Purified water was added to each dentifrice composition shown in Table 5 to provide an aqueous solution of dentifrice composition having a concentration of 30% by mass, and the human teeth were immersed in each aqueous solution of dentifrice composition in a room at 25° C. for 24 hours. Thereafter, the teeth were washed with ion exchange water and the brightness was measured by the following method. Herein, the dentifrice composition was used in the form of the aqueous solution of a concentration 30% by mass because the composition was diluted with the saliva in the oral cavity by brushing of teeth and therefore the tests were performed with the assumption of such dilution.

(Measurement Method of Brightness)

For measurement of the brightness, a method was used in which the surface reflected light intensity was measured by image analysis utilizing polarized light. As an apparatus for taking an evaluation image, one was used where a digital single-lens reflex camera Nikon D70 as a camera, Ai AF Micro-Nikkor 105 mm F2.8D as a lens, and Wireless Remote Speedlight SB-R200 for stroboscopic light emission (all manufactured by Nikon Corporation) were disposed in combination. A plastic polarizing plate (manufactured by Edmund Optics Inc.) was arranged in front of a light emission portion of Speedlight and the lens so that the transmission axes were crossed at a 30 degree angle, and an image was taken. The average brightness of a highlight portion was determined by use of Adobe Photoshop CS3 (manufactured by Adobe Systems Software Ireland Ltd.) with respect to the image taken. A larger numerical value of brightness means higher gloss. The brightness of the human teeth was measured before the treatment of the teeth with the aqueous solution of dentifrice composition, {(b* after the treatment)−(b* before the treatment)}. A value of b* closer to 0 means less yellowish and more increased whiteness, and a smaller value of Δb*, namely, a larger absolute value of Δb* means more increased whiteness.

TABLE 5

|     |     | Example 8 | Example 10 | Example 11 | Example 15 | Comparative Example 10 | Comparative Example 13 |
| --- | --- | --- | --- | --- | --- | --- | --- |
| (A) | Phytic acid (50% aqueous solution) | 0.6 | 0.6 | 0.6 | 0.6 | 0.6 | 0.6 |
| (B) | Sodium monofluorophosphate | 0.72 | 0.72 | 0.72 | 0.72 | 0.72 | 0.72 |
|     | Sodium fluoride |  |  |  | 0.01 |  | 0.105 |
|     | Sodium anhydrous pyrophosphate (*1) | 0.02 | 0.04 | 0.02 | 0.02 | 0.40 | 0.02 |
|     | Zinc oxide |  |  | 0.0006 |  |  |  |
|     | Sodium hydroxide liquid (48% aqueous solution) | Adjusted | Adjusted | Adjusted | Adjusted | Adjusted | Adjusted |
| (D) | Glycerin | 8 | 8 | 8 | 8 | 8 | 8 |
|     | Erythritol | 5 | 5 | 5 | 5 | 5 | 5 |
|     | Sorbitol liquid (70% aqueous solution) | 32 | 32 | 32 | 32 | 32 | 32 |
|     | Xylitol | 30 | 30 | 30 | 30 | 30 | 30 |
|     | Sodium lauryl sulfate | 1.5 | 1.5 | 1.5 | 1.5 | 1.5 | 1.5 |
| (C) | Sodium carboxymethylcellulose | 0.22 | 0.22 | 0.22 | 0.22 | 0.22 | 0.22 |
|     | Polyethylene glycol (PEG-600) | 3 | 3 | 3 | 3 | 3 | 3 |
|     | Thickening silica (*2) | 5.0 | 5.0 | 5.0 | 5.0 | 5.0 | 5.0 |
|     | Abrasive silica (*3) | 5.0 | 5.0 | 5.0 | 5.0 | 5.0 | 5.0 |
|     | Purified water | Balance | Balance | Balance | Balance | Balance | Balance |
|     | Flavor | 1.0 | 1.0 | 1.0 | 1.0 | 1.0 | 1.0 |
| Total |  | 100.0 | 100.0 | 100.0 | 100.0 | 100.0 | 100.0 |
| Amount of water |  | 17 | 17 | 17 | 17 | 17 | 17 |
| PH |  | 6.0 | 6.0 | 6.0 | 6.0 | 6.0 | 6.0 |
| (A) (Amount in terms of phytic acid) |  | 0.30 | 0.30 | 0.30 | 0.30 | 0.30 | 0.30 |
| (B) Amount in terms of fluorine atoms (ppm) |  | 1000 | 1000 | 1000 | 1000 | 1000 | 1000 |
| Amount of sodium fluoride in terms of fluorine atoms (ppm) |  | — | — | — | 48 | — | 500 |
| (A)/(B) |  | 0.417 | 0.417 | 0.417 | 0.417 | 0.417 | 0.417 |
| Pyrophosphoric acid (amount in terms of acid) |  | 0.013 | 0.027 | 0.013 | 0.013 | 0.268 | 0.013 |
| Molar amount of polyvalent metal cation relative to (A), (-fold mol) |  | — | — | 0.016 | — | — | — |
| Amount in terms of acid (% by mass) of polyphosphoric acid or salt thereof relative to (A) (amount in terms of phytic acid) |  | 4.5 | 8.9 | 4.5 | 4.5 | 89.2 | 4.5 |
| Friction feeling |  | 1 | 2 | 1 | 2 | 2 | 2 |
| Feeling of astringency |  | 1 | 2 | 2 | 1 | 1 | 1 |
| Black tea stain (Δb*) |  | 8.2 | 8.8 | 8.3 | 7.8 | 12 | 9.2 |
| Whitening (Δb*: teeth extracted) |  | −2.6 | −2.6 | −1.9 | −2.7 | −0.6 | −1.8 |
| Gloss (Δbrightness: teeth extracted) |  | 10 | 8 | 6 | 10 | −2 | 3 |
| Surface observation by SEM |  | Smooth | Smooth | Smooth | Smooth | Slightly rough | Rough surface |

(*1): Tetrasodium pyrophosphate
(*2): SYLOPURE 25 (Fuji Silysia Chemical Ltd., amount of oil absorption 310 mL/100 g)
(*3): SORBOSIL AC77 (PQ Corporation, amount of oil absorption 129 mL/100 g)

extracted and after the treatment with each dentifrice composition, (brightness after treatment−brightness before treatment) was then calculated as the Δ brightness, and evaluation by the value of the Δ brightness was then performed. A larger numerical value of the Δ brightness means a more increase in gloss.

<<Evaluation of Whitening Effect>>

The treatment method of the teeth extracted was performed in the same manner as in the evaluation of the gloss-imparting effect, and the color difference before and after the treatment, (Δb), was measured with respect to the human teeth extracted, before and after the treatment (human teeth after the treatment: human teeth after immersion in an aqueous solution of dentifrice composition having a concentration of 30% by mass for 24 hours and cleaning with ion exchange water). An image taken by use of a digital camera D1x (manufactured by Nikon Corporation) and a white flash light source (manufactured by Konica Minolta, Inc.) was expressed by the L*a*b* color system by use of Adobe Photoshop (manufactured by Adobe Systems Software Ireland Ltd.), and the color (whiteness) of the teeth (teeth extracted) was evaluated by using the value of b*. The Δb* means a difference in b* before and after the treatment It was confirmed from the results in Table 4 and Table 5 that, in Comparative Example 13 where sodium fluoride was contained in an amount of 500 ppm in terms of fluorine atoms, crystal adhesion to the surface of teeth was observed, roughness due to such crystal adhesion caused the surface of teeth not to be smooth, the gloss-imparting effect was low, and furthermore the suppressing effect on stain adhesion was also low. It was also confirmed that, in Comparative Example 10 where polyphosphoric acid or a salt thereof (pyrophosphoric acid or a salt thereof) was contained in an amount of even about 89% by mass in terms of acid relative to the amount of the component (A) in terms of phytic acid, the surface of teeth was not smooth, gloss rather deteriorates, the whitening effect on teeth was also lost, and the suppressing effect on stain adhesion was also low. Furthermore, also in Comparative Example 12 where zinc oxide supplying zinc as a polyvalent metal cation was contained and zinc was contained 0.27-fold mol relative to phytic acid, the following results were obtained: not only the amount of fluorine adsorption was small and the suppressing effect on stain adhesion was low, but also the feeling of astringency was very strong.

On the contrary, the following results were obtained in Examples: the friction feeling and the feeling of astringency were suppressed, the suppressing effect on stain adhesion, and fluorine adsorption performance of the component (B) were excellent, and furthermore the gloss-imparting effect and the whitening effect were also excellent. It is found from these results that, in Examples, while the component (B) was contained and the effect of fluorine adsorption to teeth was exerted, the suppressing effect on stain adhesion, the gloss-imparting effect on teeth and the whitening effect on teeth due to the component (A) were achieved.

Examples 16 to 17

Liquid oral compositions of the following formulations were prepared, respectively.

| Example 16: liquid oral composition 1 | (% by mass) |
|---|---|
| Phytic acid (50% aqueous solution) | 0.6 |
| Sodium monofluorophosphate | 0.68 |
| Erythritol | 5.0 |
| Ethanol (95%) | 5.0 |
| Sorbitol liquid (70% aqueous solution) | 4.5 |
| Polyoxyethylene (40) hydrogenated castor oil | 0.8 |
| pH Adjuster (48% sodium hydroxide liquid) | 0.25 |
| Isopropylmethylphenol | 0.02 |
| Flavor | 0.15 |
| Paraben | 0.06 |
| Sucralose | 0.006 |
| Purified water | 82.934 |
| Total | 100.000 |

(Amount in terms of fluorine atoms: 900 ppm)

| Example 17: liquid oral composition 2 | (% by mass) |
|---|---|
| Phytic acid (50% aqueous solution) | 0.6 |
| Sodium monofluorophosphate | 0.38 |
| Erythritol | 5.0 |
| Ethanol (95%) | 5.0 |
| Sorbitol liquid (70% aqueous solution) | 4.5 |
| Polyoxyethylene (40) hydrogenated castor oil | 0.8 |
| pH Adjuster (48% sodium hydroxide liquid) | 0.25 |
| Triclosan | 0.02 |
| Flavor | 0.15 |
| Paraben | 0.06 |
| Saccharin sodium | 0.01 |
| Purified water | 83.23 |
| Total | 100.000 |

(Amount in terms of fluorine atoms: 500 ppm)

What is claimed is:

1. An oral composition comprising the following components (A) and (B):
   (A) phytic acid or an alkali metal salt thereof in an amount of 0.04% by mass or more and 1% by mass or less in terms of phytic acid; and
   (B) monofluorophosphoric acid or an alkali metal salt thereof in an amount of 500 ppm or more and 1500 ppm or less in terms of fluorine atoms, wherein
   a mass ratio of the component (A) to the component (B), ((A)/(B)), is 0.1 or more and 1.4 or less,
   the composition does not comprise or comprises a fluoride ion-supplying compound (F) selected from the group consisting of sodium fluoride, potassium fluoride and ammonium fluoride in an amount of 100 ppm or less in terms of fluorine atoms,
   the composition does not comprise or comprises a polyvalent metal cation in an amount of less than 0.1-fold mol relative to the component (A),
   the composition does not comprise or comprises polyphosphoric acid or a salt thereof in an amount of 20% by mass or less in terms of polyphosphoric acid relative to the component (A), and the pH thereof is from 5.5 to 6.5.

2. The oral composition according to claim 1, wherein the composition does not comprise or comprises polyphosphoric acid or a salt thereof in an amount of 10% by mass or less in terms of acid relative to the component (A).

3. The oral composition according to claim 1, wherein the polyphosphoric acid or the salt thereof is one or more selected from the group consisting of pyrophosphoric acid, tripolyphosphoric acid, hexametaphosphoric acid, and salts thereof.

4. The oral composition according to claim 1, wherein the composition is a toothpaste composition and further comprises 0.1% by mass or more and 2% by mass or less of a binder (C).

5. The oral composition according to claim 1, further comprising 5% by mass or more and 25% by mass or less of glycerin (D).

6. The oral composition according to claim 1, wherein the polyvalent metal cation is one or more selected from the group consisting of aluminum, calcium, magnesium, iron, zinc and tin.

7. The oral composition according to claim 1, wherein a content of an abrasive comprising a polyvalent metal cation is 1% by mass or less.

8. The oral composition according to claim 1, wherein the component (A) is phytic acid or a sodium salt thereof and the component (B) is monofluorophosphoric acid or a sodium salt thereof.

9. The oral composition according to claim 1, wherein a content of a hydrogen peroxide source is 0.01% by mass or less.

10. The oral composition according to claim 1, wherein a content of an adsorbent selected from the group consisting of zeolite and activated carbon is less than 0.001% by mass.

11. The oral composition according to claim 1, wherein the composition comprises a pH adjuster which is one or more selected from the group consisting of an organic acid other than phytic acid, or a salt thereof, an inorganic acid other than pyrophosphoric acid, or a salt thereof, and a basic amino acid, and a content of the pH adjuster is 5% by mass or less relative to the amount of the component (A) in terms of phytic acid.

12. A method for adsorbing fluorine to teeth while inhibiting a stain from adhering to teeth, comprising applying the oral composition according to claim 1.

13. A method for adsorbing fluorine to teeth while inhibiting a stain from adhering to teeth and imparting gloss to teeth, comprising applying the oral composition according to claim 1.

* * * * *